United States Patent [19]

Wallace

[11] Patent Number: 5,630,428
[45] Date of Patent: May 20, 1997

[54] SPINE BOARD LIMB SUPPORTING EXTENSION

[76] Inventor: Ted T. Wallace, P.O. Box 75, Pinetown, N.C. 27865

[21] Appl. No.: 595,652

[22] Filed: Feb. 2, 1996

[51] Int. Cl.[6] ................................................ A61G 15/00
[52] U.S. Cl. ........................... 128/845; 128/870; 5/623
[58] Field of Search ............................. 128/845, 846, 128/869, 870, 878, 879, 877, 882; 602/32–39; 5/623, 624

[56] References Cited

U.S. PATENT DOCUMENTS

| | | | |
|---|---|---|---|
| 2,605,152 | 7/1952 | Krewson | 5/623 |
| 2,658,211 | 11/1953 | Bendersky | 5/623 |
| 3,650,523 | 3/1972 | Darby | 128/870 |
| 5,487,395 | 1/1996 | Strowe | 128/846 |

Primary Examiner—Michael A. Brown

[57] ABSTRACT

A spine board limb supporting extension for supporting a limb of a patient extending beyond a spine board. The inventive device includes a mounting assembly for securing to an edge of a conventionally known spine board. A support assembly is pivotally mounted to the mounting assembly for receiving and supporting a limb of a patient to immobilize and support such limb.

5 Claims, 3 Drawing Sheets

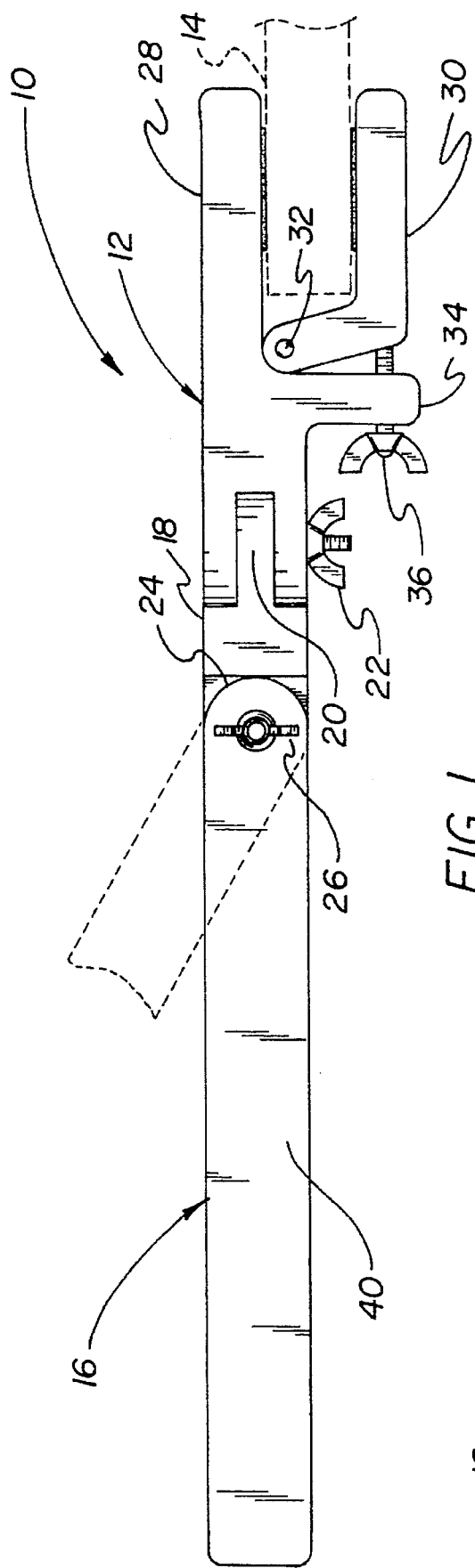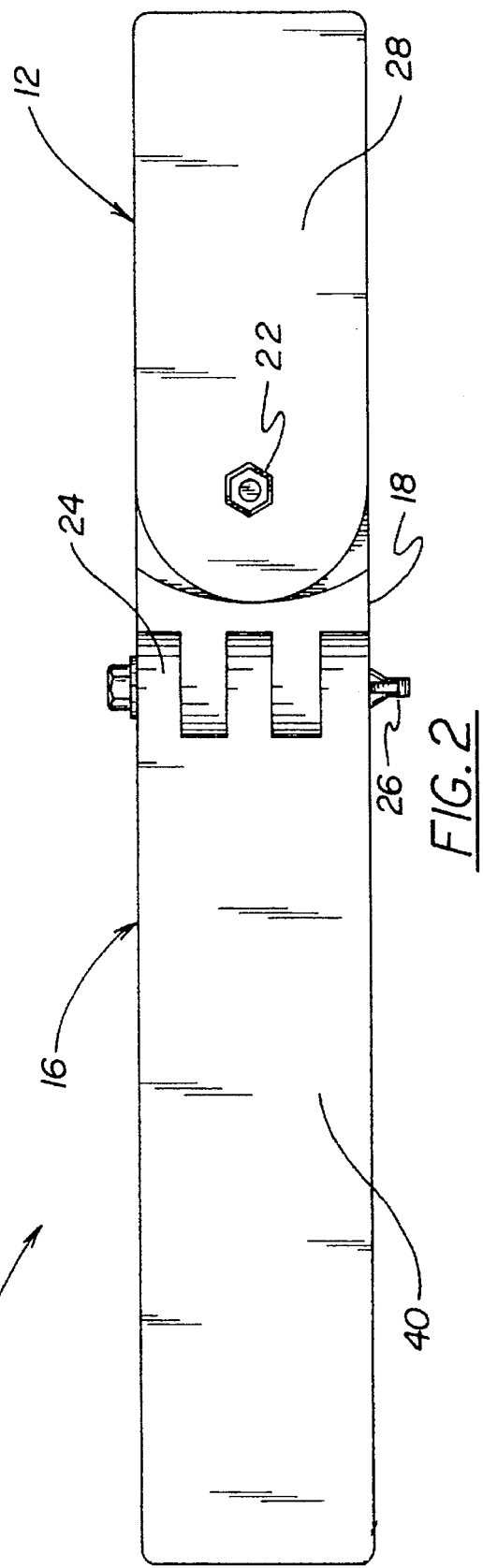

SPINE BOARD LIMB SUPPORTING EXTENSION

BACKGROUND OF THE INVENTION

1. Field of the Invention

The present invention relates to medical support structures and more particularly pertains to a spine board limb supporting extension for supporting a limb of a patient extending beyond a spine board.

2. Description of the Prior Art

The use of medical support structures is known in the prior art. More specifically, medical support structures heretofore devised and utilized are known to consist basically of familiar, expected and obvious structural configurations, notwithstanding the myriad of designs encompassed by the crowded prior art which have been developed for the fulfillment of countless objectives and requirements.

Known prior art medical support structures include U.S. Pat. No. 5,148,815; U.S. Pat. No. 4,519,106; U.S. Pat. No. 4,369,982; U.S. Pat. No. 3,707,734; U.S. Pat. No. 3,566,422; U.S. Pat. No. 5,255,303; and U.S. Pat. No. 5,263,214.

While these devices fulfill their respective, particular objectives and requirements, the aforementioned patents do not disclose a spine board limb supporting extension for supporting a limb of a patient extending beyond a spine board which includes a mounting assembly for securing to an edge of a conventionally known spine board; and a support assembly pivotally mounted to the mounting assembly for receiving and supporting a limb of a patient to immobilize and support such limb.

In these respects, the spine board limb supporting extension according to the present invention substantially departs from the conventional concepts and designs of the prior art, and in so doing provides an apparatus primarily developed for the purpose of supporting a limb of a patient extending beyond a spine board.

SUMMARY OF THE INVENTION

In view of the foregoing disadvantages inherent in the known types of medical support structures now present in the prior art, the present invention provides a new spine board limb supporting extension construction wherein the same can be utilized for supporting a limb of a patient extending beyond a spine board. As such, the general purpose of the present invention, which will be described subsequently in greater detail, is to provide a new spine board limb supporting extension apparatus and method which has many of the advantages of the medical support structures mentioned heretofore and many novel features that result in a spine board limb supporting extension which is not anticipated, rendered obvious, suggested, or even implied by any of the prior art medical support structures, either alone or in any combination thereof.

To attain this, the present invention generally comprises a spine board limb supporting extension for supporting a limb of a patient extending beyond a spine board. The inventive device includes a mounting assembly for securing to an edge of a conventionally known spine board. A support assembly is pivotally mounted to the mounting assembly for receiving and supporting a limb of a patient to immobilize and support such limb.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new spine board limb supporting extension apparatus and method which has many of the advantages of the medical support structures mentioned heretofore and many novel features that result in a spine board limb supporting extension which is not anticipated, rendered obvious, suggested, or even implied by any of the prior art medical support structures, either alone or in any combination thereof.

It is another object of the present invention to provide a new spine board limb supporting extension which may be easily and efficiently manufactured and marketed.

It is a further object of the present invention to provide a new spine board limb supporting extension which is of a durable and reliable construction.

An even further object of the present invention is to provide a new spine board limb supporting extension which is susceptible of a low cost of manufacture with regard to both materials and labor, and which accordingly is then susceptible of low prices of sale to the consuming public, thereby making such spine board limb supporting extensions economically available to the buying public.

Still yet another object of the present invention is to provide a new spine board limb supporting extension which provides in the apparatuses and methods of the prior art some of the advantages thereof, while simultaneously overcoming some of the disadvantages normally associated therewith.

Still another object of the present invention is to provide a new spine board limb supporting extension for supporting a limb of a patient extending beyond a spine board.

Yet another object of the present invention is to provide a new spine board limb supporting extension which includes a mounting assembly for securing to an edge of a conventionally known spine board; and a support assembly pivotally mounted to the mounting assembly for receiving and supporting a limb of a patient to immobilize and support such limb.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of the preferred embodiment of the spine board limb supporting extension constructed in accordance with the principles of the present invention.

FIG. 2 is a top plan view of the present invention.

Similar reference characters refer to similar parts throughout the several views of the drawings.

DESCRIPTION OF THE PREFERRED EMBODIMENT

Figure 3:
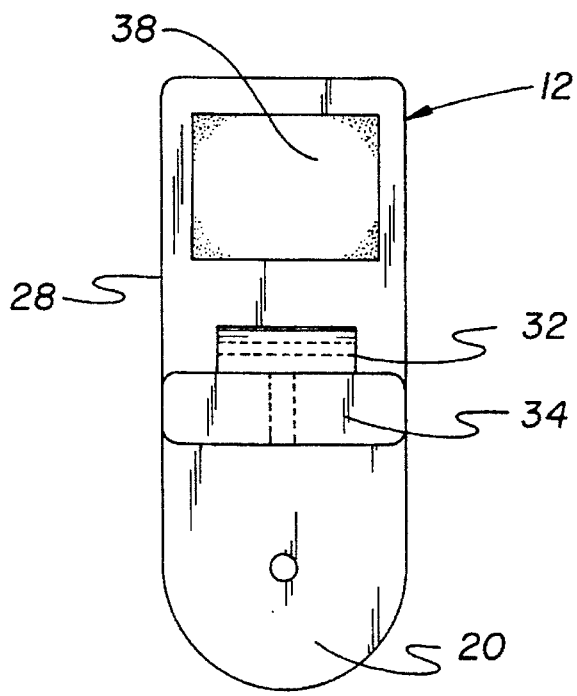
FIG. 3 is a bottom plan view of a portion of a mounting means of the invention.

With reference now to the drawings, and in particular to FIGS. 1–8 thereof, a new spine board limb supporting extension embodying the principles and concepts of the present invention and generally designated by the reference numeral 10 will be described.

More specifically, it will be noted that the spine board limb supporting extension 10 comprises a mounting means 12 for securing to an edge of a conventionally known stretcher or spine board 14 upon which injured persons are placed by emergency personnel. A support means 16 is pivotally mounted to the mounting means 12 and can be utilized to support a limb of a patient relative to the spine board 14. By this structure, limbs which would normally project beyond the relatively short spine board are given support advantageous when such limb has been injured or broken.

As shown in FIGS. 1 and 2, the present invention 10 further comprises a connecting member 18 pivotally interposed between the mounting means 12 and the support means 16. To this end, the connecting member 18 is pivotally mounted to the mounting means 12 by a lateral hinge 20 which permits the connecting member to pivot about a vertical axis. A lateral hinge fastener 22 forming a portion of the lateral hinge 20 can be manually operated to lock the lateral hinge in a desired orientation. The connecting member 18 is pivotally mounted to the support means 16 by a vertical hinge 24 which permits the connecting member to pivot about a horizontal axis oriented orthogonally relative to the vertical axis. A vertical hinge fastener 26 forming a portion of the vertical hinge 24 can be manually operated to lock the vertical hinge in a desired orientation. By this structure, the support means 16 can be pivoted about both horizontal and vertical axis into a desired position relative to the spine board 14, as illustrated in FIGS. 1 and 8, for example.

Figure 4:
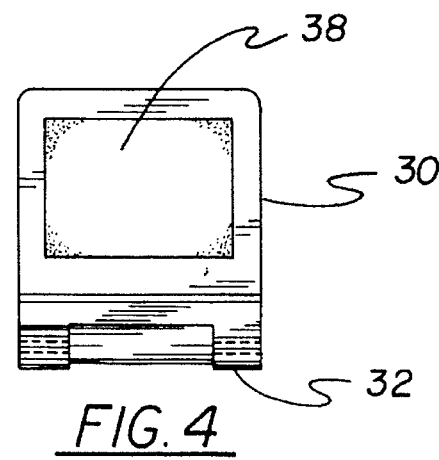
FIG. 4 is a top plan view of a further portion of the mounting means.
Figure 5:
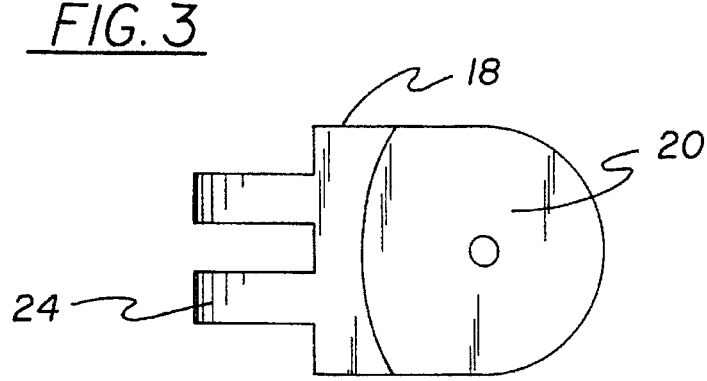
FIG. 5 is a plan view of a connecting member of the invention.

As shown in the various illustrations of FIGS. 1 through 7, the mounting means 12 comprises a first clamp arm 28 and a second clamp arm 30. A clamp hinge 32 pivotally couples the first and second clamp arms 28 and 30 together in a facing orientation. To close the clamp arms 28 and 30, an abutment plate 34 projects from the first clamp arm and receives a clamp fastener 36 directed therethrough which engages the second clamp arm 30 to pivot the second clamp arm towards the first clamp arm. By this structure, a portion of the spine board 14, as shown in FIG. 1, can be captured between the clamp arms 28 and 30 to secure the invention 10 thereto. As shown in FIGS. 3 and 4, the clamp arms may include friction pads 38 secured thereto so as to enhance frictional engagement with the spine board 14.

Figure 6:
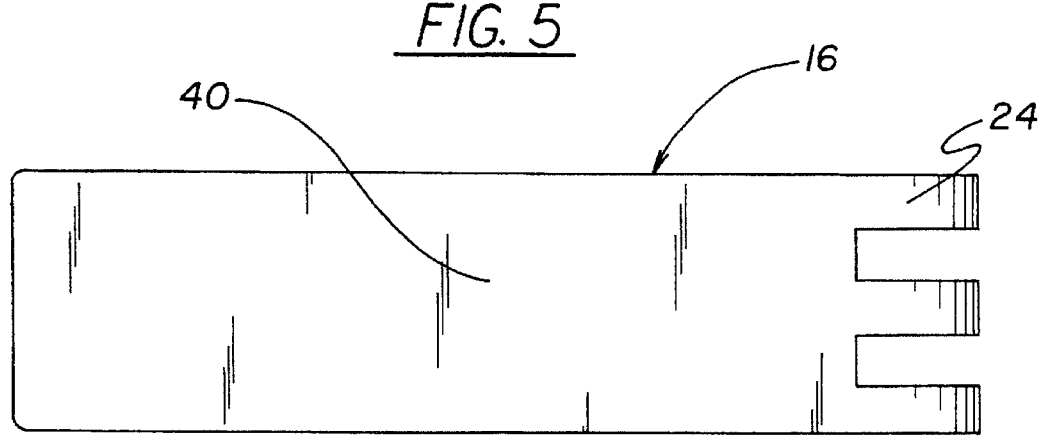
FIG. 6 is a plan view of a support means of the invention.
Figure 7:
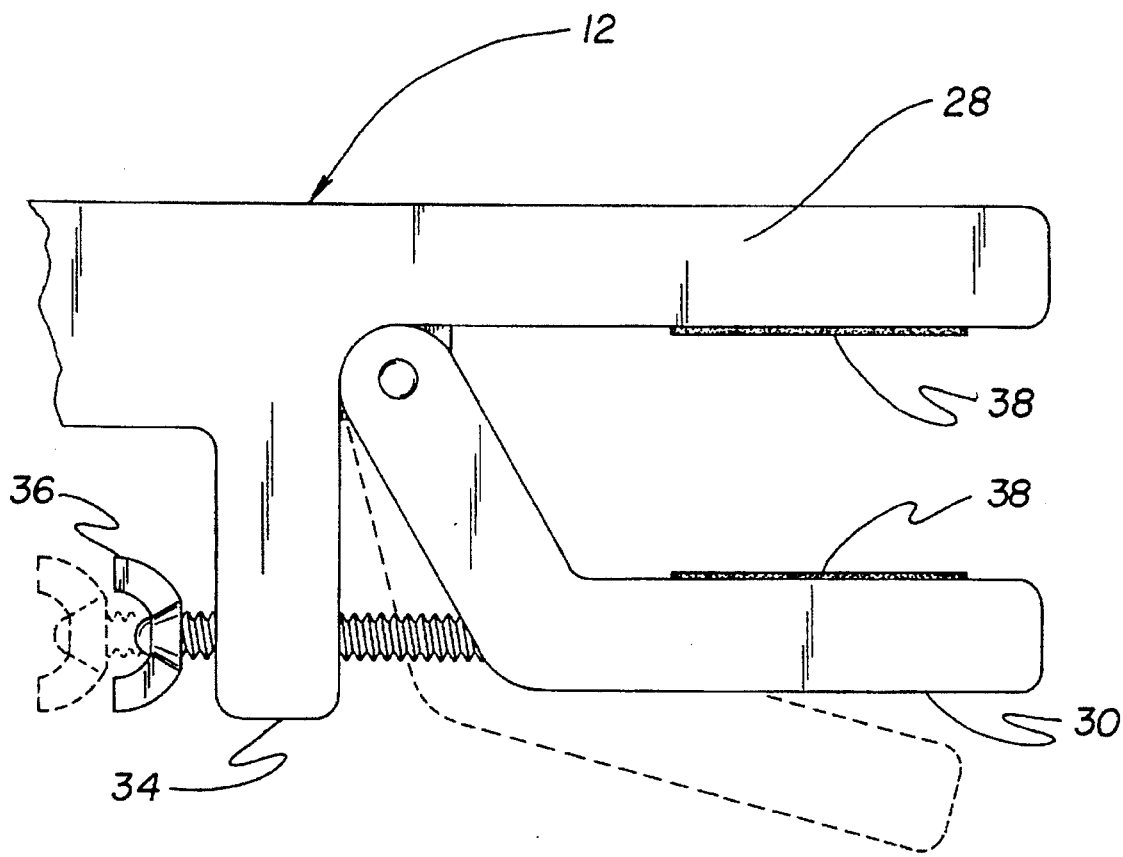
FIG. 7 is an enlarged side elevational view of the mounting means.
Figure 8:
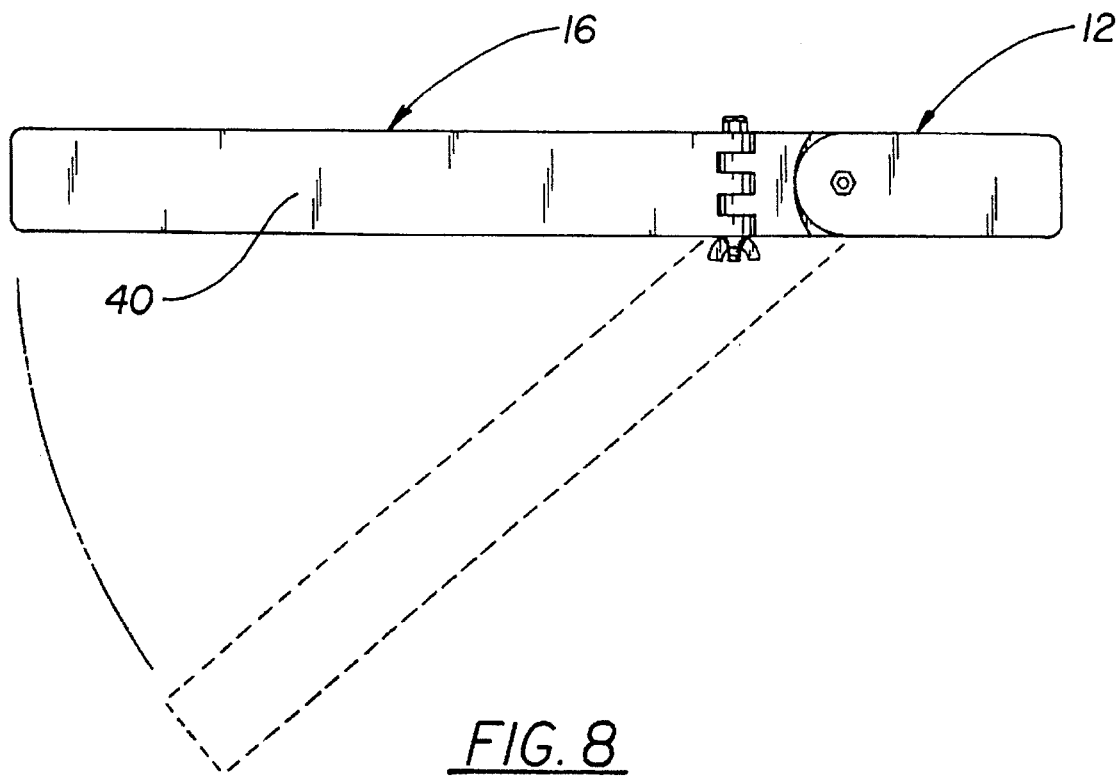
FIG. 8 is a top plan view of the invention.

As shown in FIGS. 2, 6, and 8 in particular, the support means 16 may simply comprise a planar member 40 of rectangular configuration. If desired, the planar member 40 can have straps of other limb-securing fasteners mounted thereto.

In use, the spine board limb supporting extension 10 of the present invention 10 can be easily utilized for supporting a limb of a patient extending beyond a spine board. To this end, the mounting means 12 can be secured to an edge of the spin board 14. The hinges 20 and 24 can be articulated to position the support means 16 into a position beneath a limb to be supported, and subsequently secured to support the limb beyond the spine board 14. The invention can be manufactured of a lightweight plastic or any other appropriate material.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A spine board limb supporting extension comprising:
    a mounting means for securing to an edge of a spine board;
    a support means mounted relative to the mounting means for supporting a limb of a patient relative to the spine board;
    a connecting member pivotally interposed between the mounting means and the support means, the connecting member being pivotally mounted to the mounting means by a lateral hinge which permits the connecting member to pivot about a vertical axis, the lateral hinge including a lateral hinge fastener which can be manually operated to lock the lateral hinge in a predetermined orientation, and further wherein the connecting member is pivotally mounted to the support means by a vertical hinge which permits the connecting member to pivot relative to the support means about a horizontal axis oriented orthogonally relative to the vertical axis, the vertical hinge including a vertical hinge fastener which can be manually operated to lock the vertical hinge in a predetermined orientation.

2. A spine board limb supporting extension comprising:

a mounting means for Securing to an edge of a spine board;

a support means mounted relative to the mounting means for supporting a limb of a patient relative to the sSpine board;

a connecting member pivotally interposed between the mounting means and the support means, the connecting member being pivotally mounted to the mounting means by a lateral hinge which permits the connecting member to pivot about a vertical axis, the lateral hinge including a lateral hinge fastener which can be manually operated to lock the lateral hinge in a predetermined orientation, and further wherein the connecting member is pivotally mounted to the support means by a vertical hinge which permits the connecting member to pivot relative to the support means about a horizontal axis oriented orthogonally relative to the vertical axis, the vertical hinge including a vertical hinge fastener which can be manually operated to lock the vertical hinge in a predetermined orientation; and the mounting means comprising a first clamp arm, a second clamp arm, a clamp hinge pivotally coupling the first and second clamp arms together in a facing orientation, an abutment plate projecting from the first clamp arm, and a clamp fastener directed through the abutment plate which engages the second clamp arm to pivot the second clamp arm towards the first clamp arm as the fastener is advanced through the abutment plate.

3. The spine board limb supporting extension of claim 1, wherein the support means comprises a planar member of rectangular configuration coupled to the vertical hinge.

4. A spine board limb supporting extension comprising:

a spine board;

a mounting means secured to an edge of the spine board;

a support means mounted relative to the mounting means for supporting a limb of a patient relative to the spine board;

a connecting member pivotally interposed between the mounting means and the support means, the connecting member being pivotally mounted to the mounting means by a lateral hinge which permits the connecting member to pivot about a vertical axis, the lateral hinge including a lateral hinge fastener which can be manually operated to lock the lateral hinge in a predetermined orientation, and further wherein the connecting member is pivotally mounted to the support means by a vertical hinge which permits the connecting member to pivot relative to the support means about a horizontal axis oriented orthogonally relative to the vertical axis, the vertical hinge including a vertical hinge fastener which can be manually operated to lock the vertical hinge in a predetermined orientation; and the mounting means comprising a first clamp arm, a second clamp arm, a clamp hinge pivotally coupling the first and second clamp arms together in a facing orientation, an abutment plate projecting from the first clamp arm, and a clamp fastener directed through the abutment plate which engages the second clamp arm to pivot the second clamp arm towards the first clamp arm as the fastener is advanced through the abutment plate.

5. The spine board limb supporting extension of claim 4, wherein the support means comprises a planar member of rectangular configuration coupled to the vertical hinge.

* * * * *